US006911551B2

(12) United States Patent
Stössel et al.

(10) Patent No.: US 6,911,551 B2
(45) Date of Patent: Jun. 28, 2005

(54) SPIRO COMPOUNDS BASED ON BORON OR ALUMINUM AND THE USE OF THE SAME IN THE ELECTRONICS INDUSTRY

(75) Inventors: Philipp Stössel, Frankfurt (DE); Hubert Spreitzer, Viernheim (DE); Heinrich Becker, Glashütten (DE); Jacqueline Drott, Riedstadt (DE)

(73) Assignee: Covion Organic Semiconductors GmbH (DE)

( * ) Notice: Subject to any disclaimer, the term of this patent is extended or adjusted under 35 U.S.C. 154(b) by 34 days.

(21) Appl. No.: 10/250,593

(22) PCT Filed: Dec. 20, 2001

(86) PCT No.: PCT/EP01/15177

§ 371 (c)(1),
(2), (4) Date: Oct. 23, 2003

(87) PCT Pub. No.: WO02/051850

PCT Pub. Date: Jul. 4, 2002

(65) Prior Publication Data

US 2004/0063981 A1 Apr. 1, 2004

(30) Foreign Application Priority Data

Dec. 22, 2000 (EP) .............................. 00128292

(51) Int. Cl.⁷ .............................. C07F 5/06; C07F 5/02; H01L 31/00; C09K 11/06; H01S 3/16
(52) U.S. Cl. .............................. 556/178; 568/1; 568/3; 556/170; 549/2; 549/3; 549/210; 549/213; 548/402; 548/405; 546/4; 546/10; 546/13; 544/225; 544/229; 372/41; 136/236.1; 136/237; 136/263; 252/301.18; 428/917

(58) Field of Search .................. 568/1, 3; 556/170, 556/178; 549/1, 3, 210, 213; 548/402, 405; 546/4, 10, 13; 544/225, 229; 372/41; 136/236.1, 237, 263; 252/301.18; 428/917

(56) References Cited

U.S. PATENT DOCUMENTS

| 4,539,507 A | 9/1985 | VanSlyke et al. |
| 5,151,629 A | 9/1992 | VanSlyke |
| 5,621,131 A | 4/1997 | Kreuder et al. |

FOREIGN PATENT DOCUMENTS

DE      44 36 773      4/1996

OTHER PUBLICATIONS

Tetsuya Noda et al., "A Blue–Emitting Organic Electroluminescent Device Using A Novel Emitting Amorphous Molecular Material, 5.5'–Bis(dimesitylboryl)–2.2'–bithiophene", Adv. Mater. 1999, 11, No. 4.

Primary Examiner—Porfirio Nazario-Gonzalez
(74) Attorney, Agent, or Firm—Connolly Bove Lodge & Hutz LLP

(57) ABSTRACT

The present invention relates to substituted boron or aluminum spiro compounds and their use in the electronic industry. The compounds of the invention are used as electron transport material, hole blocking material and/or as host material in organic electroluminescence and/or phosphorescence devices, as electron transport material in photocopiers, as electron acceptor or electron transport material in solar cells, as charge transport material in organic ICs (circuits) and in organic solid-state lasers or organic photodetectors.

13 Claims, 2 Drawing Sheets

Figure 1:
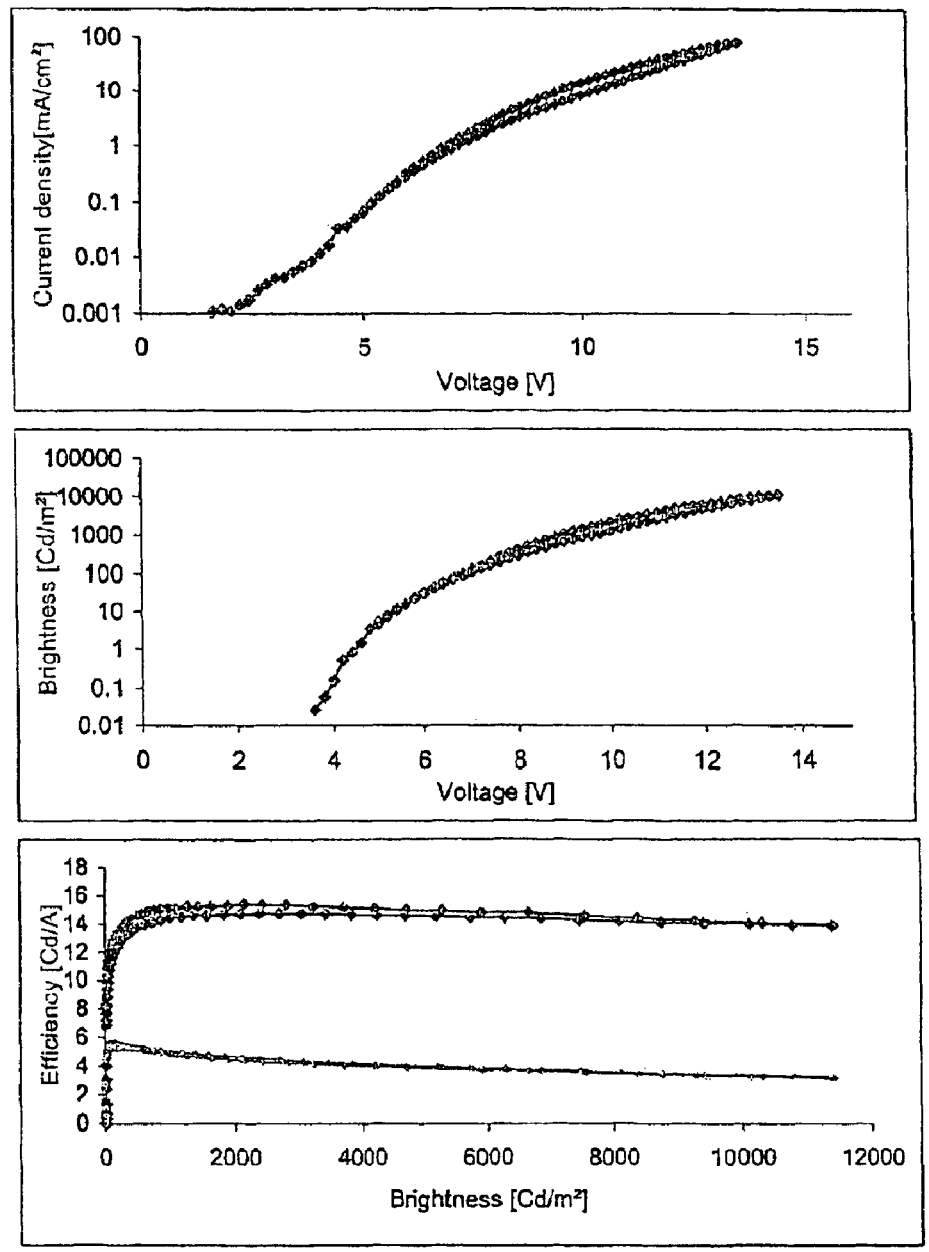

SPIRO COMPOUNDS BASED ON BORON OR ALUMINUM AND THE USE OF THE SAME IN THE ELECTRONICS INDUSTRY

The present invention relates to substituted boron or aluminum spiro compounds and their use in the electronics industry.

In a variety of different applications, which can in the broadest sense be considered parts of the electronics industry, the use of organic compounds as active components (=functional materials) has been reality for some time or is expected in the near future.

Thus, charge transport materials based on organic compounds (generally hole transport materials based on triarylamines) have been used for many years in copiers.

The use of specific semiconductive organic compounds, some of which are also capable of emission of light in the visible region of the spectrum, is just at the beginning of introduction onto the market, for example in organic electroluminescence devices.

The use of organic charge transport layers in applications such as organic integrated circuits (organic ICs) and organic solar cells has already progressed a long way, at least in the research stage, so that introduction onto the market may be expected within the next few years.

The number of further possibilities is very large, but frequently only as a modification of the above-described processes, as evidenced by the examples of organic solid-state laser diodes and organic photodetectors.

In some of these modern applications, development has sometimes already progressed a long way, but there is still, depending on the application, a tremendous need for technical improvements.

Organic electroluminescence devices and their individual components, viz. organic light-emitting diodes (OLEDs) have already been introduced on to the market, as evidenced by the commercially available automobile radios having an "organic display" from Pioneer. Further such products will be introduced shortly.

Nevertheless, considerable improvements are still necessary to make these displays truly competitive with the liquid crystal displays (LCDs) which dominate the market at present, or to make it possible for the LCDs to be overtaken.

One relative development which has appeared in the last two years is the use of organometallic complexes which display phosphorescence instead of fluorescence [M. A. Baldo, D. F. O'Brian, Y. You, A. Shoustikov, S. Sibley, M. E. Thompson, S. R. Forrest, Nature, 1998, 395, 151–154; M. A. Baldo, S. Lamansky, P. E. Burrows, M. E. Thompson, S. R. Forrest, Applied Physics Letters, 1999, 75, 4–6], and which can as a result, for theoretical statistical reasons, give a three- to four-fold improvement in the energy and power efficiency. However, whether this new development will become established depends greatly on whether corresponding device compositions which can apply these advantages (triplet emission=phosphorescence compared to singlet emission=fluorescence) in OLEDs can be found. Requirements include, for example, a long operating life, a high heat resistance, a low use and operating voltage so as to make mobile applications possible, to name only a few.

The general structure of organic electroluminescence devices is described, for example, in U.S. Pat. No. 4,539,507 and U.S. Pat. No. 5,151,629.

An organic electroluminescence device usually consists of a plurality of layers which are preferably applied on top of one another by means of vacuum methods. These layers are specifically:

1. a support plate=substrate (usually glass or a plastic film);
2. a transparent anode (usually indium-tin oxide, ITO);
3. a hole injection layer (=HIL): e.g. one based on copper phthalocyanine (CuPc), conductive polymers such as polyaniline (PANI) or polythiophene derivatives (e.g. PEDOT);
4. a hole transport layer (=HTL): usually based on triarylamine derivatives;
5. an emission layer (=EML): this layer can sometimes coincide with the layers 4 or 6, but is usually made up of host molecules doped with fluorescent dyes or phosphorescent dyes;
6. an electron transport layer (=ETL): mostly based on aluminum tris-8-hydroxyquinoxalinate ($AlQ_3$);
7. an electron injection layer (=EIL): this layer can sometimes coincide with the layer 6 or a small part of the cathode is specially treated or specially deposited;
8. a cathode: use is here generally made of metals, metal combinations or metal alloys having a low work function, e.g. Ca, Ba, Mg, Al, In, Mg/Ag.

This overall device is naturally appropriately (depending on the application) structured, provided with contacts and finally hermetically sealed, since the life of such devices is generally reduced drastically in the presence of water and/or air.

On application of an appropriate voltage, holes from the anode and electrons from the cathode are injected into the device and these meet in the device to produce an excited state. This can decay with emission of light. This light is radiated through the transparent anode. In some applications, it can be useful to invert the arrangement, i.e. to use a (semi)transparent cathode when the anode is, for example, applied to a nontransparent substrate (for example a silicon chip).

For the new phosphorescent OLED devices, it can also be advantageous to insert further thin layers which block individual charge carriers (e.g. hole blocking layers=HBLs).

In any case, the individual OLED will emit light which has a color determined by the EML. In this way, it is possible to generate the three basic colors (blue, green, red) depending on the EML.

Suitable combinations of various individual OLEDs then makes it possible to produce a variety of devices starting from individual light-emitting diodes through simple segmented displays and more complicated matrix displays to full-color, large-area displays/VDUs.

In the case of the abovementioned OLED device, the functional materials mentioned above have been or are being intensively optimized.

However, it is conspicuous that $AlQ_3$ is used virtually exclusively as ETL in all devices. This compound is, as mentioned above, frequently also used as host material for the EML. Although many attempts have been made to replace this compound by other substances, these have not succeeded to date.

$AlQ_3$ still represents the best compromise for the various requirements. Thus, the compound has a high thermal stability (glass transition temperature $T_g \sim 180°$ C.) combined with an obviously usable band position and an acceptable fluorescence quantum efficiency in the solid (about 40%). However, a negative aspect is the intrinsic color (absorption: yellow) of the compound which specifically in the case of blue OLEDs can lead to fluorescence absorption and reemission to produce color shifts. This is a serious disadvantage in the abovementioned device structure in which the light is emitted through the cathode, i.e. through the ETL as well. In this case, blue OLEDs can be produced only with a serious deterioration in efficiency or color shade.

The usability of $AlQ_3$ in the new phosphorescent OLEDs has also not been finally clarified.

A further disadvantage of the use of $AlQ_3$ is the instability in the presence of holes [cf., for example, Z. Popovic et al., Proceedings of SPIE, 1999, 3797, 310–315] which is now known from the literature and which can lead to problems in the device in long-term use.

A critical practical disadvantage of $AlQ_3$ is the strongly hygroscopic nature of this compound. $AlQ_3$ which is synthesized and stored under normal conditions still contains one molecule of water in addition to the hydroxyquinoline ligands per molecule of complex [cf., for example: H. Schmidbaur et al., Z. Naturforsch. 1991, 46b, 901–911]. This is extremely difficult to remove. For use in OLEDs, $AlQ_3$ therefore has to be laboriously purified in a complicated, multistage sublimation process and subsequently stored and handled in the absence of water under a protective gas atmosphere. Furthermore, wide fluctuations in the quality of individual $AlQ_3$ batches and a poor shelf life have been found (S. Karg, E-MRS conference May 30–Jun. 2, 2000, Strasbourg).

There is therefore a need for alternative compounds which, firstly, match the requirement profile of $AlQ_3$ and, secondly, make simpler handling possible.

It has now surprisingly been found that particular boron or aluminum compounds display excellent properties when used as ETL, as HBL or as host material in the EML. Use in the new phosphorescent OLED devices in particular is very advantageous.

These compounds are subject matter of the present invention. Compared to $AlQ_3$, the compounds have the following properties:

1. They are colorless or virtually colorless; this means that their UV/VIS absorption in the wavelength range from 400 to 700 nm is negligible. This has the advantage that, especially in the case of blue OLEDs, they do not lead to a color shift or a reduction in efficiency. A further advantage is naturally their use as host or ETL material in inverted (cf. above) device geometries.

2. When the boron or aluminum compounds of the invention are used as ETL material in electroluminescence devices, they lead to high efficiencies which are, in particular, independent of the current densities used. This makes very good efficiencies possible even at high current densities.

3. The boron or aluminum compounds of the invention have a significantly higher oxidation stability than $AlQ_3$. For use in appropriate devices, this can lead to a significant increase in the operating life.

4. The boron or aluminum compounds of the invention display no noticeable hygroscopic behavior; Storage for a number of days or weeks in the presence of air and water vapor leads to no changes in the substances. An addition reaction of water with the compounds cannot be detected. This naturally has the advantage that the substances can be purified, transported, stored and prepared for use under simpler conditions. In contrast to operations using $AlQ_3$, use does not have to take place entirely under protected gas.

5. The boron or aluminum compounds of the invention can be prepared in a readily reproducible fashion in reliable high purity and display no fluctuation between batches.

6. The boron or aluminum compounds of the invention also have a high thermal stability which in some cases can be superior to that of $AlQ_3$. However, this is not mentioned here as a decisive advantage, but it should be merely pointed out that this property, too, is achieved very satisfactorily by the boranes or organoaluminum compounds.

7. The boron or aluminum compounds of the invention have an excellent solubility in organic solvents. These materials can therefore also be processed from solution by means of coating or printing techniques. This property is also advantageous in the customary processing by vaporization, so that cleaning of the plants or the masks used is made considerably easier.

Only a few incidences of the use of boron-containing compounds in OLED devices have hitherto been described. Only Y. Shirota (e.g. Y. Shirota et al., Adv. Mater. 1999, 11, 283) describes a bisthiophene-bisborane compound in OLEDs. However, use is made here of, inter alia, exciplex formation with hole transport layers, which indicates morphological instability.

However, the boron or aluminum compounds of the invention are bulky and thus display suppression of exciplex formation and at the same time form very stable organic glasses.

To be able to be used as electroluminescence materials, the boron or aluminum compounds are applied in the form of a film to a substrate, generally by known methods with which those skilled in the art are familiar, e.g. vacuum deposition or from solution by spin coating or using various printing methods (e.g. inkjet printing, offset printing, etc.).

Apart from the use of the boranes or aluminum compounds of the invention in OLED devices, these compounds can be used in a very broad range of applications in electronics. Thus, the compounds of the invention can be used in the following devices:

1. Use in photocopiers as electron transport layer.
2. Use in organic solar cells as electron acceptor or electron transport material.
3. Use in organic ICs as charge transport layer.
4. Use in further applications, some of which have been mentioned above, e.g. organic solid-state lasers or organic photodetectors.

The invention accordingly provides substituted boron or aluminum spiro compounds of the formula (I),

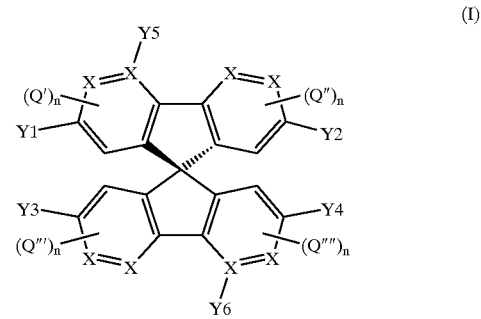

(I)

where the symbols and indices have the following meanings:

Q', Q'', Q''', Q'''' are identical or different on each occurrence and are each CN, F, Cl or a straight-chain or branched or cyclic alkyl or alkoxy group which has from 1 to 20 carbon atoms and in which one or more nonadjacent $CH_2$ groups may be replaced by —O—, —S—, —CO—, —COO—, —O—CO—, —$NR^1$—, —$(NR^2R^3)^+$-$A^-$ or —$CONR^4$— and one or more H atoms may be replaced by F, or an aryl or heteroaryl group which has from 4 to 14 carbon atoms and may be substituted by one or more nonaromatic radicals Q';

A⁻ is a singly charged anion or its equivalent;

$R^1, R^2, R^3, R^4$ are identical or different and are each H or an aliphatic or aromatic hydrocarbon radical having from 1 to 20 carbon atoms;

n are identical or different and are each 0, 1, 2, 3;

X is —CH— or N;

Y1 to Y6: include at least two identical or different substituents of the formula (II) and the remaining Y1 to Y6 in the positions of the aromatic which are not occupied by formula (II) are identical or different substituents Q' or H, where the formula (II) is

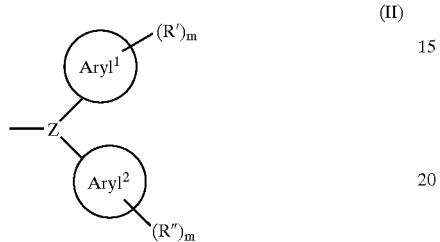

(II)

where

Aryl¹, Aryl² are identical or different on each occurrence and are each phenyl, 1- or 2-naphthyl, 1-, 2- or 9-anthracenyl, 2-, 3- or 4-pyridinyl, 2-, 4- or 5-pyrimidinyl 2-pyrazinyl, 3- or 4-pyridazinyl, 2-, 3-, 4-, 5-, 6-, 7- or 8-quinolinyl, 2- or 3-thienyl, 2- or 3-pyrrolyl, 2- or 3-furanyl and 2-(1,3,4-oxadiazol)yl;

R', R" are identical or different on each occurrence and are each CN, F, Cl or a straight-chain or branched or cyclic alkyl or alkoxy group which has from 1 to 20 carbon atoms and in which one or more nonadjacent CH₂ groups may be replaced by —O—, —S—, —CO—, —COO—, —O—CO—, —NR¹—, —(NR²R³)⁺A⁻ or —CONR⁴— and one or more H atoms may be replaced by F, or an aryl or heteroaryl group which has from 4 to 14 carbon atoms and may be substituted by one or more nonaromatic radicals R';

A⁻ is a singly charged anion or its equivalent;

$R^1, R^2, R^3, R^4$ are identical or different and are each H or an aliphatic or aromatic hydrocarbon radical having from 1 to 20 carbon atoms;

m are identical or different and are each 0, 1, 2, 3, 4, 5;

Z is boron or aluminum.

The boron or aluminum Spiro compounds of the invention are very suitable for use as electron transport layers in electroluminescence components and as photoconductors in electrooptical components. Furthermore, they are very suitable as electroluminescence materials. They can likewise be used as host materials together with a variety of dopants. Both dyes and triplet emitters are suitable for this purpose. In these applications, the compounds of the invention display, for example, the advantage that they have a constant brightness in long-term operation even at elevated temperatures (e.g. heating to 130° C. for a number of hours). Furthermore, the voltage to be applied for a given brightness remains largely constant. It is thus not necessary to adjust the voltage in long-term operation in order to maintain an initial brightness. This advantage becomes particularly noticeable in battery operation, since in this case the maximum possible voltage is greatly restricted for economic reasons.

Likewise, devices comprising the boron or aluminum spiro compounds of the invention have a long life and a high EL efficiency.

Preference is given to boron or aluminum spiro compounds having a carbocyclic spiro skeleton in which X=—CH—, as shown in formula (III),

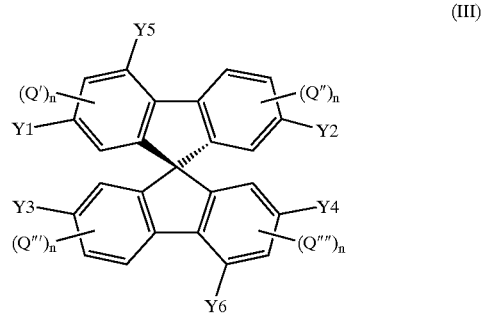

(III)

where the remaining symbols and indices are as defined under formula (I).

Particular preference is given to boron or aluminum spiro compounds having a carbocyclic spiro skeleton of the formula (III) in which the aryl substituents Aryl¹, Aryl² in the substituents Y1 to Y6 are each phenyl, 1-naphthyl, 2-naphthyl or 9-anthracenyl.

The stability, in particular to oxidation, is particularly high when the aryl substituents Aryl¹, Aryl² in the formula (II) are substituted in the ortho and ortho' positions by alkyl, alkyloxy or aryl.

Particular preference is given to compounds in which the symbol Z represents boron.

Further preference is given to the corresponding compounds in which the substituents Y5 and Y6 are each Q' or H.

Accordingly, very particular preference is given to boron spiro compounds of the formula (IV) which bear ortho-, ortho'- and para-substituted diphenylboryl radicals as substituents Y1 to Y4:

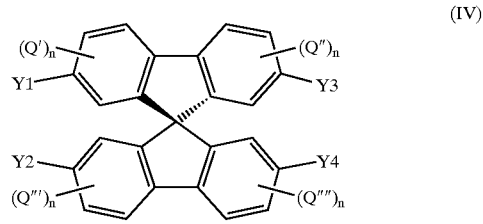

(IV)

where the symbols and indices have the following meanings:

Y1 to Y4 include at least two identical or different substituents of the formula (V) and the remaining Y1 to Y4 in the positions of the aromatic which are not occupied by formula (V) are identical or different substituents Q' or H, where the formula (V) is

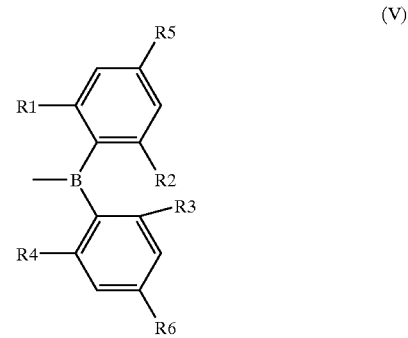

(V)

where
    n are identical or different and are each 0, 1, 2;
    R1, R2, R3, R4 are identical or different and are each an alkyl, alkyloxy or aryl radical having from 1 to 20 carbon atoms and
    R5, R6 are identical or different and are each H, CN, F, Cl, Br, I, a straight-chain, branched or cyclic alkyl or alkoxy group, a thioalkyl or thioaryl group, a nitro group, a diarylamino or dialkylamino group or an ester, amide or carboxyl group, where the alkyl, alkoxy or aryl groups have from 1 to 20 carbon atoms.
The further symbols and indices are as defined under formula (I) and formula (II).

Most preferred spiro compounds of the formula (IV) have from two to four identical substituents Y1 to Y4.

Here, further substituents (R5, R6) having an electron donor or electron acceptor action in the para position relative to the boron have a particularly strong influence on the electrical and electrooptical properties of the spiro compound, so that the electrooptical properties can be tailored by appropriate selection of these substituents.

Spiro compounds of the formulae (I) to (V) are obtained, for example, from 9,9'-spirobifluorene whose synthesis is described, for example, by G. G. Clarkson, M. Gomberg, J. Am. Chem. Soc. 52 (1930), 2881. The synthesis can then be carried out, for example, by selective halogenation of the 9,9'-spirobifluorene (R. Wu, J. S. Schumm, D. L. Pearson, J. M. Tour, J. Org. Chem., 1996, 61, 6906–6921) and subsequent reaction of the 2,7,2',7'-tetrabromo-9,9'-spirobifluorene obtained in this way with a metal (e.g. Li, Mg), a metal alloy (e.g. Li—Al alloy) or a metal compound (n-, sec-, tert-butyllithium, Grignard compound) and subsequent salt-metathetic reaction with an organoboron-halogen or organoaluminum-halogen compound. The reaction of a lithiated spiro compound with diarylboron or diarylaluminum halides has been found to the useful here.

The preparation of unsymmetrical spiro compounds of the formulae (I) to (VI) can be carried out, for example, by reaction of a biphenyl derivative substituted in the 2 position with a functionalized fluorenone (e.g. 2,7-dibromofluorenone). The 2'-, 7'-, 4- and 4' positions can then be functionalized further by means of various reagents, for example halogen derivatives as acid chlorides.

The synthesis and properties of the above-described boron and aluminum compounds of the invention is illustrated by the following examples, but is not restricted thereto.

1. Synthesis of Boron and Aluminum Spiro Compounds

The following syntheses were carried out, up to the work-up, in carefully dried reaction vessels under a dry pure nitrogen atmosphere or argon atmosphere using carefully dried solvents. The starting materials were either purchased from ALDRICH (n-butyllithium 1.6 molar in n-hexane, tert-butyllithium 1.7 molar in n-hexane) and used without further purification or prepared by literature methods (2,7, 2',7'-tetrabromo-9,9'-spirobifluorene: R. Wu, J. S. Schumm, D. L. Pearson, J. M. Tour, J. Org. Chem., 1996, 61, 6906–6921, fluorodimesitylborane: A. Pelter, B. Singaram, L. Warren, J. W. Wilson, Tetrahedron 1993, 49, 2965–2978).

EXAMPLE 1

Synthesis of 2,7-di-tert-butyl-2',7'-bis(dimesitylboryl)-9,9'-spirobifluorene (S-DDMB)

13.1 ml (21 mmol) of a 1.6 M solution of n-butyllithium in n-hexane were added dropwise to a well-stirred suspension of 5.86 g (10 mmol) of 2,7-di-tert-butyl-2',7'-dibromo-9,9'-spirobifluorene in 120 ml of absolute THF which had been cooled to −78° C. over a period of 20 minutes at such a rate that the temperature of the reaction mixture did not exceed −65° C. The suspension was stirred for another 1 hour at −78° C. and a solution of 5.63 g (21 mmol) of fluorodimesitylborane in 50 ml of absolute THF was then added dropwise over a period of 20 minutes at such a rate that the temperature of the reaction mixture did not exceed −65° C.

The reaction mixture was allowed to warm to room temperature over a period of 12 hours while stirring. The THF was subsequently removed on a rotary evaporator, the yellow, semisolid residue was taken up in 200 ml of dichloromethane, the organic phase was washed twice with water and dried over magnesium sulfate. After the desiccant had been filtered off, the organic phase was evaporated to dryness. The yellow crude product (about 8.5–9.0 g, purity according to HPLC: 92–95%) was repeatedly recrystallized from toluene/ethanol until a purity of 99.8% as determined by HPLC had been reached. The yield, at a purity of 99.8% as determined by HPLC, was 5.0–6.0 g, corresponding to 55–65%.

$^1$H NMR (CDCl$_3$): [ppm]=7.84 (d, H-4, H-5, $^3J_{HH}$=7.8 Hz, 2 H), 7.55 (d, H-4', H-5', $^3J_{HH}$=7.8 Hz, 2 H), 7.47 (br. d, H-3, H-6, $^3J_{HH}$=7.8 Hz, 2 H), 7.29 (dd, H-3', H-6', $^3J_{HH}$=7.8 Hz, $^4J_{HH}$=1.9 Hz, 2 H), 6.93 (br. s, H-1, H-8, 2 H), 6.70 (br. s, H-1', H-8', H-mes, 10 H), 2.22 (s, CH$_3$, 12 H), 1.81 (s, CH$_3$, 24 H), 1.14 (s, CH$_3$, 18 H). Thermal data (from DSC): T$_g$~155° C., T$_m$=327° C.

EXAMPLE 2

Synthesis of 2,7,2',7'-tetrakis(dimesitylboryl)-9,9'-spirobifluorene (S-TDMB)

56.5 ml (96 mmol) of a 1.7 M solution of tert-butyllithium in n-hexane were added dropwise to a well-stirred suspension of 6.32 g (10 mmol) of 2,7, 2',7'-tetrabromo-9,9'-spirobifluorene in 200 ml of absolute THF which had been cooled to −78° C. over a period of 20 minutes at such a rate that the temperature of the reaction mixture did not exceed −65° C. The suspension was stirred for another 1 hour at −78° C. and a solution of 11.80 g (48 mmol) of fluorodimesitylborane in 100 ml of absolute THF was then added dropwise over a period of 20 minutes at such a rate that the temperature of the reaction mixture did not exceed −65° C.

The reaction mixture was allowed to warm to room temperature over a period of 12 hours while stirring. The THF was subsequently removed on a rotary evaporator, the yellow, semisolid residue was taken up in 400 ml of dichloromethane, the organic phase was washed twice with water and dried over magnesium sulfate. After the desiccant had been filtered off, the organic phase was evaporated to dryness. The yellow crude product (about 12.5–13.0 g, purity according to HPLC: 92–95%) was repeatedly recrystallized from dioxane and chloroform until a purity of 99.9% as determined by HPLC had been reached. The yield, at a purity of 99.9% as determined by HPLC, was 9.0–11.0 g, corresponding to 70–85%.

$^1$H NMR (CDCl$_3$): [ppm]=7.73 (d, H-4, H-4', H-5, H-5', $^3J_{HH}$=7.8 Hz, 4 H), 7.45 (dd, H-3, H-3', H-6, H-6', $^3J_{HH}$=7.8 Hz, $^4J_{HH}$=1.1 Hz, 4 H), 6.96 (br. s, H-1, H-1', H-8, H-8', 4 H), 6.70 (br. s, H-mes, 16 H), 2.26 (s, CH$_3$, 24 H), 1.83 (s, CH$_3$, 48 H). Thermal data (from DSC): T$_g$~210° C., T$_m$=387° C.

2. Production and Characterization of Organic Electroluminescence Devices Comprising Compounds According to the Invention The production of LEDs was carried out by the general method outlined below.

Naturally, it had to be adapted in each particular case to the respective circumstances (e.g. variation of the layer thicknesses to achieve optimal efficiency or color).

General Method of Producing OLEDs

After the ITO-coated substrates (e.g. glass support, PET film) have been cut to the correct size, they are cleaned in a number of cleaning steps in an ultrasonic bath (e.g. soap solution, Millipore water, isopropanol).

They are dried with the aid of an $N_2$ gun and stored in a desiccator. Before vapor deposition of the organic layers, the substrates are treated by means of an ozone plasma apparatus for about 20 minutes. It can be advisable to use a polymeric hole injection layer as first organic layer. This is generally a conjugated, conductive polymer, e.g. a polyaniline derivative (PANI) or a polythiophene derivative (e.g. PEDOT from BAYER). This is then applied by spin coating.

The organic layers are applied in order by vapor deposition in a high-vacuum unit. The thickness of the respective layer and the vapor deposition rate are precisely monitored or set with the aid of a crystal oscillator.

It is also possible, as described above, for individual layers to consist of more than one compound, i.e. in general a host material doped with a guest material. This is achieved by covaporization from two or more sources.

Electrodes are then applied to the organic layers. This is generally achieved by thermal vapor deposition (Balzer BA360 or Pfeiffer PL S 500). The transparent ITO electrode as anode and the metal electrode (e.g. Ca, Yb, Ba—Al) as cathode are subsequently applied and the device parameters are determined.

EXAMPLE 1

Using a procedure analogous to the abovementioned general method, a green-emitting OLED having the following structure was produced:

| | |
|---|---|
| PEDOT | 20 nm (applied by spin coating from water; PEDOT purchased from BAYER AG; poly(3,4-ethylenedioxy)-2,5-thiophene) |
| MTDATA | 20 nm (vapor deposited; MTDATA purchased from SynTec; tris-4,4',4"-(3-methylphenylphenylamino)triphenylamine) |
| S-TAD | 20 nm (vapor deposited; S-TAD prepared as described in WO99/12888; 2,2',7,7'-tetrakis(diphenylamino)spirobifluorene) |
| CBP | 40 nm (vapor deposited; CBP purchased from ALDRICH and further purified, finally sublimed twice; 4,4'-bis(N-carbazolyl)biphenyl) doped with 6% IrPPy |
| IrPPy | (co-vapor deposited; IrPPy synthesized and purified by a method similar to that of R. J. Watts et al., Inorg. Chem. 1991, 30, 1687; fac-tris(2-phenylpyridyl)iridium(III)) |
| BCP | 8 nm (vapor deposited; BCP purchased from ABCR, used as received; 2,9-dimethyl-4,7-diphenyl-1,10-phenanthroline) |
| S-TDMB | 10 nm (cf. Synthesis Example 2) |
| Yb | 150 nm as cathode |

This OLED was characterized in a standard manner; the most important EL data are shown in FIG. 1. A tremendous advantage of this OLED is the extreme flatness of the efficiency curve, which means that very high efficiencies are still achieved at very high brightnesses (e.g. 10 000 Cd/m$^2$). This is of great importance for use in passive matrix-operated displays.

EXAMPLE 2

Using a procedure similar to the abovementioned general method, a blue-emitting OLED having the following structure was produced:

| | |
|---|---|
| PEDOT | 20 nm |
| MTDATA | 20 nm |
| S-TAD | 20 nm |
| S-DPBVi | 30 nm (vapor deposited; synthesized by a method analogous to that of H. Spreitzer et al., Proc. SPIE Vol. 3797, 316; 2,2',7,7'-tetrakis(2,2-diphenylvinyl)spirobifluorene) |
| S-TDMB | 10 nm |
| Yb | 100 nm as cathode |

Figure 2:
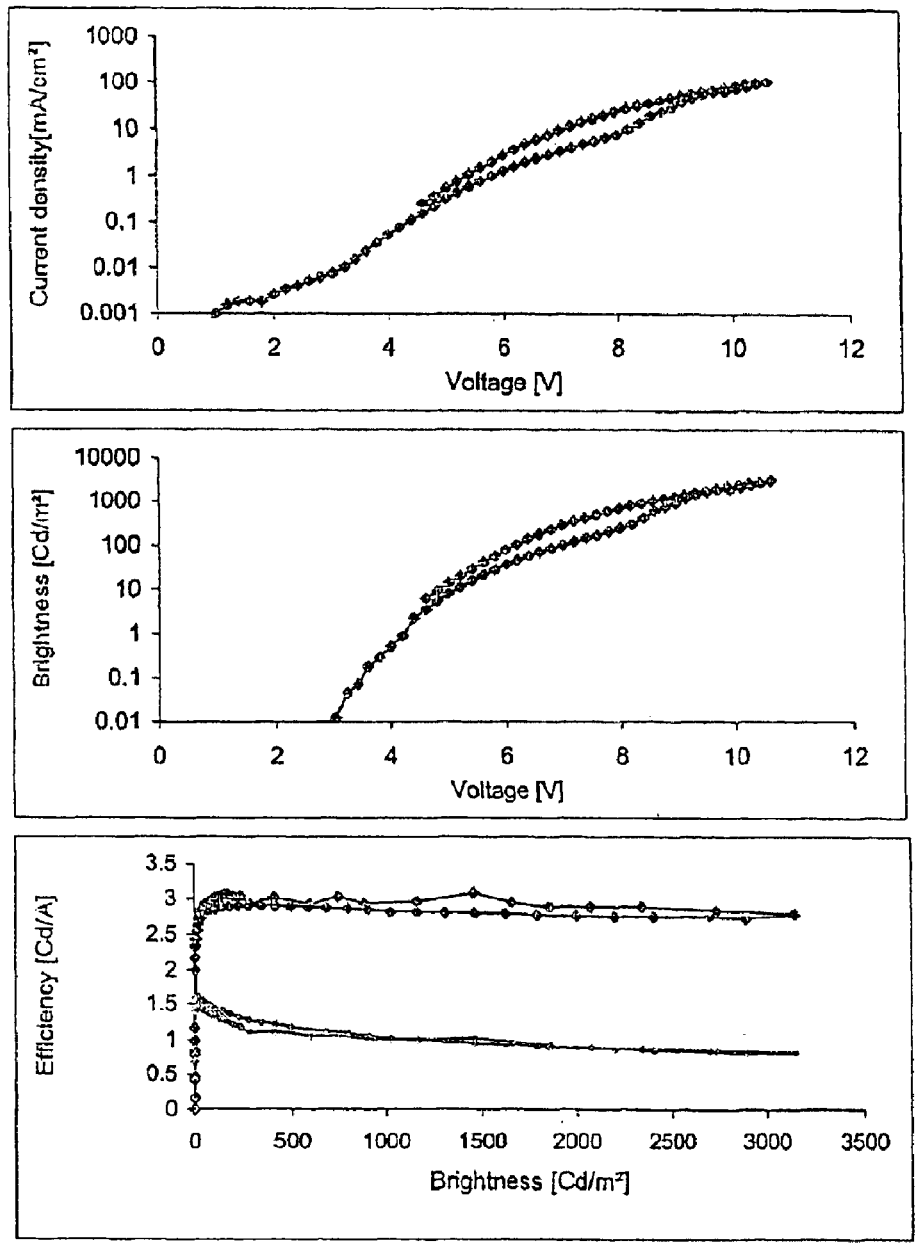

This OLED was characterized in a standard manner; the most important EL data are shown in FIG. 2. This undoped OLED has I-V EL characteristics equivalent to an analogous device in which S-TDMB had been replaced by AlQ$_3$ (20 nm). However, a significant advantage is the fact that the spectrum of the emission is narrower and the color coordinates are thus shifted in the blue direction (AlQ$_3$ OLED: x=0.14, y=0.16; S-TDMB OLED: x=0.12, y=0.14). This is, firstly, an advantage in full color applications (i.e. the color in the display is more brilliant) and, secondly, it also means that the quantum efficiency is higher since the blue shift of the emission means a lower brightness (in candela!).

What is claimed is:

1. A compound of the general formula (I),

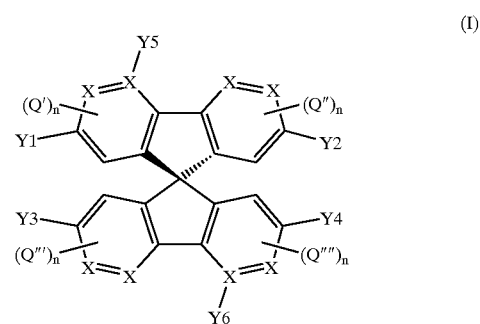

where the symbols and indices have the following meanings:

Q', Q", Q''', and Q"" are identical or different on each occurrence and are each CN, F, Cl or a straight-chain or branched or cyclic alkyl or alkoxy group which has from 1 to 20 carbon atoms and in which one or more nonadjacent CH$_2$ groups is optionally replaced by —O—, —S—, —CO—, —COO—, —O—CO—, —NR—, —(NR$^2$R$^3$)$^+$-A$^-$ or —CONR$^4$— and one or more H atoms is optionally replaced by F, or an aryl or heteroaryl group which has from 4 to 14 carbon atoms and is optionally substituted by one or CN, F, Cl or a straight-chain or branched or cyclic alkyl or alkoxy group which has from 1 to 20 carbon atoms and in which one or more nonadjacent CH$_2$ groups is optionally replaced by —O—, —S—, —CO—, —COO—, —O—CO—, —NR$^1$—, ~(NR$^2$R$^3$)$^+$-A$^-$ or —CONR$^4$— and one or more H atoms is optionally replaced by F;

A$^-$ is a singly charged anion or its equivalent;

R$^1$, R$^2$, R$^3$, and R$^4$ are identical or different and are each H or an aliphatic or aromatic hydrocarbon radical having from 1 to 20 carbon atoms;

n are identical or different and are each 0, 1, 2, 3;

X is —CH— or N;

Y1 to Y6: include at least two identical or different substituents of the formula (II) and the remaining Y1 to Y6 in the positions of the aromatic which are not occupied by formula (II) are identical or different substituents Q' or H, where the formula (II) is

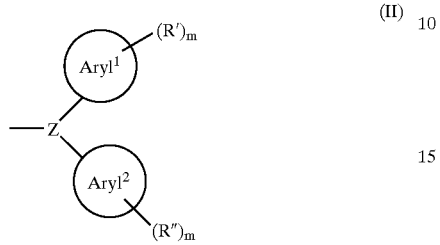

where

Aryl$^1$ and Aryl$^2$ are identical or different on each occurrence and are each phenyl, 1-naphthyl, 2-naphthyl, 1-anthracenyl, 2-anthracenyl, 9-anthracenyl, 2-pyridinyl, 3-pyridinyl, 4-pyridinyl, 2-pyrimidinyl, 4-pyrimidinyl, 5-pyrimidinyl, 2-pyrazinyl, 3-pyridazinyl, 4-pyridazinyl, 2-quinolinyl, 3-quinolinyl, 4-quinolinyl, 5-quinolinyl, 6-quinolinyl, 7-quinolinyl, 8-quinolinyl, 2-thienyl, 3-thienyl, 2-pyrrolyl, 3-pyrrolyl, 2-furanyl, 3-furanyl or 2-(1,3,4-oxadiazol)yl;

R' and R" are identical or different on each occurrence and are each CN, F, Cl or a straight-chain or branched or cyclic alkyl or alkoxy group which has from 1 to 20 carbon atoms and in which one or more nonadjacent CH$_2$ groups is optionally replaced by —O—, —S—, —CO—, —COO—, —O—CO—, —NR$^1$—, —(NR$^2$R$^3$)$^+$A$^-$ or —CONR$^4$— and one or more H atoms is optionally replaced by F, or an aryl or heteroaryl group which has from 4 to 14 carbon atoms and which is optionally substituted by one or more CN, F, Cl or a straight-chain or branched or cyclic alkyl or alkoxy group which has from 1 to 20 carbon atoms and in which one or more nonadjacent CH$_2$ groups is optionally replaced by —O—, —S—, —CO—, —COO—, —O—CO—, —NR$^1$—, —(NR$^2$R$^3$)$^+$A$^-$ or —CONR$^4$— and one or more H atoms is optionally replaced by F;

A$^-$ is a singly charged anion or its equivalent;

R$^1$, R$^2$, R$^3$, and R$^4$ are identical or different and are each H or an aliphatic or aromatic hydrocarbon radical having from 1 to 20 carbon atoms;

m are identical or different and are each 0, 1, 2, 3, 4, or 5;

Z is boron or aluminum.

2. The compound as claimed in claim 1, wherein X is —CH—.

3. The compound as claimed in claim 1, wherein the aryl substituents Aryl$^1$ and Aryl$^2$ in the substituents Y1 to Y6 are each phenyl, 1-naphthyl, 2-naphthyl or 9-anthracenyl.

4. The compound as claimed in claim 1, wherein Z is boron.

5. The compound as claimed in claim 1, wherein the substituents Y5 and Y6 are Q' and hydrogen.

6. The compound of the formula (IV)

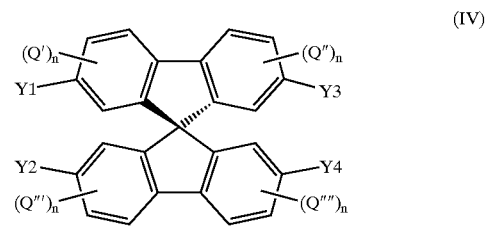

wherein

Y1 to Y4 include at least two identical or different substituents of the formula (V) and the remaining Y1 to Y4 in the positions of the aromatic which are not occupied by formula (V) are identical or different substituents Q' or hydrogen, where the formula (V) is

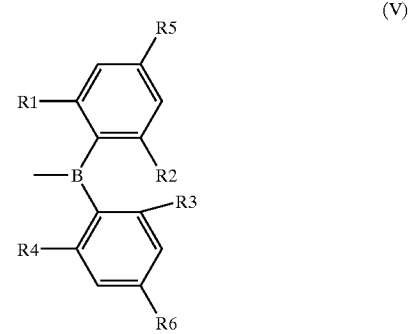

wherein n are identical or different and are each 0, 1 or 2;

R1, R2, R3 and R4 are identical or different and are each an alkyl, alkyloxy or aryl radical having from 1 to 20 carbon atoms and R5 and R6 are identical or different and are each H, CN, F, Cl, Br, I, a straight-chain, branched or cyclic alkyl, a straight-chain, branched or cyclic alkoxy group, a thicalkyl group, thioaryl group, a nitro group, a diarylamino group, dialkylamino group, an ester group, amide group, carboxyl group, wherein the alkyl, alkoxy or aryl groups have from 1 to 20 carbon atoms.

7. The compound as claimed in claim 6, wherein two, three or four of the radicals Y1 to Y4 are identical.

8. An organic electroluminescence and/or phosphorescence device which comprises the compound as claimed in claim 1.

9. An electron transport layer (ETL), hole blocking layer (HBL) and/or as host material in organic electroluminescence and/or phosphorescence device which comprises the compound as claimed in claim 1.

10. An electron transport material in photocopiers which comprises the compound as claimed in claim 1.

11. An electron acceptor or electron transport material in solar cells which comprises the compound as claimed in claim 1.

12. A charge transport material in organic ICs (circuits) which comprises the compound as claimed in claim 1.

13. An organic solid-state laser or organic photodetector which comprises the compound as claimed in claim 1.

* * * * *

UNITED STATES PATENT AND TRADEMARK OFFICE
CERTIFICATE OF CORRECTION

PATENT NO.     : 6,911,551 B2
DATED          : June 28, 2005
INVENTOR(S)    : Philipp Stössel et al.

Page 1 of 1

It is certified that error appears in the above-identified patent and that said Letters Patent is hereby corrected as shown below:

Column 10,
Line 53, delete "-NR-" and insert -- -NR$^1$- --.

Signed and Sealed this

Eighth Day of November, 2005

JON W. DUDAS
*Director of the United States Patent and Trademark Office*